(12) United States Patent
Correia

(10) Patent No.: US 8,987,172 B2
(45) Date of Patent: Mar. 24, 2015

(54) HERBICIDE CONTAINING GLYPHOSATE AND A SURFACTANT CONSISTING ESSENTIALLY OF A POLYALKOXYLATED ALKYLAMINE WHEREIN THE ALKYL GROUP IS BRANCHED

(76) Inventor: Pedro Manuel Brito da Silva Correia, Estoril (PT)

( * ) Notice: Subject to any disclaimer, the term of this patent is extended or adjusted under 35 U.S.C. 154(b) by 430 days.

(21) Appl. No.: 13/494,493

(22) Filed: Jun. 12, 2012

(65) Prior Publication Data

US 2012/0252675 A1   Oct. 4, 2012

Related U.S. Application Data

(63) Continuation-in-part of application No. 12/484,212, filed on Jun. 14, 2009, now abandoned, and a continuation-in-part of application No. 12/541,989, filed on Aug. 17, 2009, now abandoned.

(51) Int. Cl.
| | | |
|---|---|---|
| *A01N 25/00* | (2006.01) | |
| *C07C 213/00* | (2006.01) | |
| *A01N 57/20* | (2006.01) | |
| *C07C 215/00* | (2006.01) | |
| *C07C 217/00* | (2006.01) | |

(52) U.S. Cl.
CPC ...................................... *A01N 57/20* (2013.01)
USPC .......................... 504/206; 504/116.1; 564/505

(58) Field of Classification Search
CPC ... A01N 2300/00; A01N 33/12; A01N 37/52; A01N 57/12; A01N 59/26
USPC ................................ 504/116.1, 206; 564/505
See application file for complete search history.

(56) References Cited

U.S. PATENT DOCUMENTS

| | | | |
|---|---|---|---|
| 3,457,312 A | 7/1969 | Miller et al. | |
| 5,180,414 A * | 1/1993 | Darchy et al. | ................ 504/206 |
| 5,258,359 A | 11/1993 | Kassebaum et al. | |
| 5,389,598 A * | 2/1995 | Berk et al. | ..................... 504/206 |
| 5,658,853 A | 8/1997 | Kassebaum et al. | |
| 5,663,117 A | 9/1997 | Warner | |
| 5,912,209 A | 6/1999 | Kassebaum et al. | |
| 6,063,733 A | 5/2000 | Berger et al. | |
| 6,365,551 B1 | 4/2002 | Wright et al. | |
| 6,734,141 B2 | 5/2004 | Humble et al. | |
| 7,316,990 B2 | 1/2008 | Tank et al. | |

FOREIGN PATENT DOCUMENTS

| | | |
|---|---|---|
| EP | 1541023 A2 | 6/2005 |
| WO | WO-9921424 A1 | 5/1999 |
| WO | WO-2006034459 A1 | 3/2006 |

* cited by examiner

*Primary Examiner* — Rebecca Prouty
*Assistant Examiner* — Danielle Sullivan

(57) ABSTRACT

The present invention relates to glyphosate formulations (herbicides) containing glyphosate and a surfactant consisting essentially of a branched alkylamine where the nitrogen atom in the alkylamine is connected to a branched alkyl group and one, two or three chains of alkylene oxide units (e.g., ethylene oxide units and/or propylene oxide units, including copolymers of ethylene oxide and propylene oxide units).

2 Claims, No Drawings

HERBICIDE CONTAINING GLYPHOSATE AND A SURFACTANT CONSISTING ESSENTIALLY OF A POLYALKOXYLATED ALKYLAMINE WHEREIN THE ALKYL GROUP IS BRANCHED

CROSS-REFERENCE TO RELATED APPLICATIONS

The present application is a continuation-in-part of commonly owned and abandoned U.S. patent application Ser. No. 12/484,212, filed Jun. 14, 2009, and Ser. No. 12/541,989, filed Aug. 17, 2009. The entire disclosures of both of these applications (i.e., Ser. Nos. 12/484,212 and 12/541,989) are specifically incorporated herein by reference.

BACKGROUND OF THE INVENTION (1) Field of the Invention

The present invention relates to glyphosate formulations (herbicides) containing glyphosate and a surfactant consisting essentially of a branched alkylamine where the nitrogen atom in the alkylamine is connected to a branched alkyl group and one, two or three chains of alkylene oxide units (e.g., ethylene oxide units and/or propylene oxide units, including copolymers of ethylene oxide and propylene oxide units).

(2) Description of the Related Art

Important concerns on health and environment exist worldwide on the consequences of the application of herbicides and other pesticides for food production.

The need to strongly increase the yields per hectare and the quality a food are important factors influencing the use of pesticides, mainly considering the problems of hunger.

In order to find a compromise between these two opposite factors, the European Commission published directive 91/414, the US Government published FIFRA, and FAO and the World Health Organisation are preparing a Guideline on the Use of Pesticides to be approved by all countries.

The objective is to harmonize the rules on the sales authorization of pesticides.

It is unacceptable that the World Trade Organisation creates a free market, if food originated in some countries is exported to other countries, where the residues of pesticides in the food do not comply with existing rules in the importing countries.

Since glyphosate was patented by the U.S. company Monsanto, alkylamine polyethoxylated (also known as polyethoxylated amines or polyethoxylated alkylamines) as surfactants were included in the first patents. The alkyl group of the alkylamine polyethoxylated surfactants taught in these patents was a linear alkyl group.

The length of the linear alkyl chain was subject to optimising efforts and the use of other surfactants mixed with alkylamine polyethoxylated surfactants was also tried. The use of other families of compounds like alkylphosphonates polyethoxylated, polysiloxanes, sarcosinates, betain polyethoxylates and many other compounds have been patented. (See U.S. Pat. Nos. 5,258,359; 5,658,853; 5,663,117; 5,912,209; and 6,734,141 as well as European Patent No. 1,541,023).

In our U.S. patent application Ser. No. 12/484,212, we presented the new glyphosate formulation containing branched alkylamines polyethoxylated, and described their advantages in comparison to earlier formulations.

In our U.S. patent application Ser. No. 12/541,989, we described herbicides consisting of a glyphosate formulation containing as a surfactant a branched alkylamine where the nitrogen atom is connected to a chain of propylene oxide monomers (i.e., polypropylenoxide) or to a copolymer of ethylene oxide and propylene oxide monomers, and described their advantages in comparison to earlier formulations.

Branched alkyl alcohol polyethoxylated with alkyl chains with less carbon atoms like 10-12 have been earlier used together with the linear alkylamine polyethoxylated in order to reduce the micelle formation and therefore the surface tension. In this way the content of the classical long chain alkylamines polyethoxylated could be reduced.

In the present invention, we are using the branched alkyl groups in the amine polyalkoxylated (e.g., polyethoxylated) itself. Branches in the alkyl chain create steric hindrance to micelle formation. Micelles consisting of surfactant molecules reduce the amount of surfactant available to decrease the surface tension.

Because of miscibility limitations, the content of the branched alcohol polyethoxylated is limited.

We found that a branched alkyl amine, polyethoxylated mixed or not with a branched alkyl alcohol polyethoxylated makes possible a reduction of isopropylamine, which is a co-formulant, and avoids the micelle formation, which is most important. The speed of penetration of the solution in water of the glyphosate formulation through the membranes of the leaves of the weeds is therefore strongly improved, therefore improving the efficacy of the formulation as a herbicide.

SUMMARY OF THE INVENTION

Glyphosate is by far the most sold pesticide worldwide, and its production volumes were even increased by the introduction in many countries of the genetically modified seeds resistant to glyphosate.

A surfactant for such high volume herbicide has to present a high performance and availability but must have a low cost.

A good surfactant allows a reduction of the dose per hectare, and improves the speed of absorption of the water solution of the glyphosate formulation by the leaves of the weeds. This makes possible the application of glyphosate under rainy weather conditions.

In fact, even if it rains a short time after the application of a rapidly absorbed herbicide, there will be no more herbicide on the leaves, because it was absorbed.

In its broadest aspects, the present invention relates to a herbicide containing glyphosate and a surfactant consisting essentially of a polyalkoxylated alkylamine wherein the alkyl group is branched. In preferred embodiments, the polyalkoxylated portion of the alkylamine is composed of polyethylenoxide (i.e., chains, of ethylene oxide units) and/or polypropylenoxide (i.e., chains of propylene oxide units), including copolymers of ethylene oxide and propylene oxide units.

As discussed later herein, preferred embodiments of the present invention include glyphosate formulations (herbicides) containing glyphosate and a surfactant consisting essentially of a branched alkylamine where the nitrogen atom in the alkylamine is connected to a branched alkyl group and one, two or three chains of polyethylenoxide (i.e., chains of ethylene oxide units) and/or polypropylenoxide (i.e., chains of propylene oxide units)) including copolymers of ethylene oxide and propylene oxide units. The term "units", as used herein, is equivalent in meaning to the term "monomers".

The glyphosate herbicide of the present invention exhibits among other things, an improved surface tension as compared to previously used glyphosate herbicides. The glyphosate herbicide of the present invention demonstrates improved rainfastness (better control of weeds in conditions where rain closely follows application of the herbicide) in comparison to other glyphosate herbicide formulations.

DETAILED DESCRIPTION OF THE INVENTION

It is well known from surfactant chemistry that the surfactant molecules act by making a monolayer around the particle to be dispersed or emulsified in water.

A surfactant molecule consists of a lipophilic part attracted by the particle to be emulsified and a hydrophilic part which is oriented in the opposite direction.

The surfactant orients itself on the water surface with the lipophilic part of the molecules oriented to the air, and the hydrophilic part directed to the center of the water drop. The surfactant builds like a fat thin layer on the water surface. This fat thin layer behaves like a membrane. If the intermolecular forces between molecules of the membrane are reduced by the steric hindrance caused by branched alkyl groups, the membrane becomes weaker and smaller droplets form.

Based on this mechanism it is possible to reduce the size of droplets when spraying a water solution of an herbicide. Besides this effect, the droplets in contact with the surface of the leaves are not spherical (which causes the droplets to roll off the surface of the leaves and fall to the ground), but instead are spread out on the surface of the leaves, because the attraction of the solution molecules, to the leaves is bigger than the attraction of the molecules of the solution among themselves. This causes the droplets to grip the leaves better and also allows more of the solution to penetrate the surface of the leaves and be absorbed by the plant in a shorter period of time.

Some surfactant molecules have the tendency to come together in clusters building micelles, instead of going apart from each other and increasing the interaction with the solvent and reducing its surface tension.

The formation of micelles reduces the amount of surfactant available to reduce the surface tension.

On the other side, glyphosate is an amino acid, therefore presenting an amphoteric character, and an isoelectric point in water solutions. The solubility of glyphosate in water is only about 1.5% by weight at room temperature and the pH of this solution (i.e., a solution of 1.5% by weight of glyphosate in water) is about 2. In order to increase the solubility of glyphosate in water, it is necessary to increase the pH of the solution by adding an alkaline hydroxide or an amine.

It was found that the addition of a low molecular weight amine (e.g., like isopropylamine), increases the amount of glyphosate which can be dissolved in water containing a surfactant. However, the low molecular weight amine has itself and alone no herbicide action and is therefore a pollutant.

Using a surfactant containing an amine makes possible to reduce the content of the low molecular weight amine. (e.g., isopropylamine), which anyhow is used to increase the pH and improve the solubility of the glyphosate in water.

A longer chain, especially a longer linear chain, of the alkyl group of the surfactant normally reduces its biodegradability and increases its toxicity.

Use of branched alkyl groups like propylheptyl in the surfactant (e.g., so that the surfactant is propylheptylamine polyethoxylated or polypropoxylated) present a favourable behavior in the daphnia test (i.e., less toxic for daphnia, therefore better water quality), in the test of algal growth inhibition (i.e., less toxic for algae, therefore better water quality), and in biodegradability (i.e., faster disappearance of residues of glyphosate from the environment, therefore better water or soil quality), as compared to the linear C16-C18 alkyl groups from natural fat.

According to our Portuguese Patent 2005/103 372, we presented a formulation containing a mixture of branched or even cyclized alkyl groups as alcohol polyethoxylated mixed with long chain alkylamines (i.e., long chain linear alkylamines) polyethoxylated.

We proposed in our U.S. patent application Ser. No. 12/484,212 to use the branched alkyl groups in the amine polyethoxylated itself.

We further proposed in out U.S. patent application Ser. No. 12/541,989 to use instead of polyethoxylated chains, also polypropoxylated chains or copolymers of ethylene oxide and propylene oxide monomers.

In the present application, we describe glyphosate formulations containing a surfactant(s) consisting essentially of polyalkoxylated alkylamines (e.g., polyethoxylated alkylamines and/or polypropoxylated alkylamines) wherein the alkyl group of the alkylamine is branched and the alkylene oxide chains (e.g., ethylene oxide and/or propylene oxide chains) that make up the polyalkoxylate (e.g., polyethoxylate and/or polypropoxylate) portion of the alkylamines is/are attached to the nitrogen atom of the amine. As described in more detail below, the ethylene oxide and/or propylene oxide chains that are attached to the nitrogen atom of the amine can also form chains that are copolymers constituted by both ethylene oxide and propylene oxide monomers.

Thus, the present invention also includes herbicides containing glyphosate and a surfactant consisting essentially of a branched alkylamine where the nitrogen atom in the alkylamine is connected to one, two or three chains of alkylene oxide units (e.g., ethylene oxide units and/or propylene oxide units, including a copolymer of ethylene oxide and propylene oxide units).

In the broadest aspect of the present invention, the surfactant in the glyphosate formulation has the structure, of Formula I or II (below):

Formula I

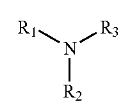

Formula II 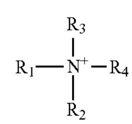 wherein $R_2$ is a $C_{8-20}$ branched alkyl, preferably a $C_{8-16}$ branched alkyl;

$R_2$ is a polyalkoxylate group, preferably a polyethoxylate group, a polypropoxylate group or a copolymer of ethylene oxide and propylene oxide units;

$R_3$ is a linear alkyl, a branched alkyl or a polyalkoxylate group (e.g., a polyethoxylate group, a polypropoxylate group or a copolymer of ethylene oxide and propylene oxide units);

$R_4$ is a linear alkyl, a branched alkyl or a polyalkoxylate group (e.g., a polyethoxylate group, a polypropoxylate group or a copolymer of ethylene oxide and propylene oxide units); and when $R_4$ is present. (thus creating an ion), the ion is neutralized by the glyphosate anion or a halogen (preferably chlorine).

The term "polyalkoxylate group" as used herein, means a group having the structure:

Formula IIIA or

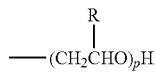

Formula IIIB where R is hydrogen or an alkyl group having from 1 to 3 carbon atoms and p is an integer from 2 to 20. Examples of acceptable polyalkoxylate groups are polyethoxylates, polypropoxylates, polybutoxylates and polypentoxylates.

It should be noted that the polyalkoxylates of the present invention can also have chains composed of random units of Formula IIIA and IIIB. For example,

When the surfactant has the structure of Formula I or II, $R_1$ must be a branched alkyl group. $R_2$ must be a polyalkoxylate group, $R_3$ and $R_4$ can both be alkyl groups, or can both be polyalkoxylate groups, or one can be an alkyl group and the other a polyalkoxylate group. For example, as long as $R_3$ and $R_4$ fall within the definitions provided above for the structures of Formula I or II, they can be the same or different (i.e., groups $R_2$, $R_3$ and $R_4$ can all be identical, or two of these groups can be identical and the third is different, or all three groups can be different from one another). For exemplary purposes only (not intended to be limiting), groups $R_2$, $R_3$ and $R_4$ can all be polyethoxylates having the structure $(CH_2CH_2O)_2H$. Alternatively, groups $R_1$ and $R_3$ can both be polyethoxylates having the structure $(CH_2CH_2O)_2H$ and $R_4$ can be a linear alkyl, a branched alkyl or a polyalkoxylate group (e.g., a polyethoxylate group, a polypropoxylate group or a copolymer of ethylene oxide and propylene oxide units) that is different than $(CH_2CH_2O)_2H$. Alternatively, group $R_2$ can be a polyethoxylate having the structure $(CH_2CH_2O)_2H$, $R_3$ could be a polyethoxylate having the structure $(CH_2CH_2O)_4H$ and $R_4$ could be a linear alkyl, a branched alkyl or a polyalkoxylate group (e.g., a polyethoxylate group, a polypropoxylate group, or a copolymer of ethylene, oxide and propylene oxide units) that is different than either $(CH_2CH_2O)_2H$ or $(CH_2CH_2O)_4H$.

Some examples of preferred polyalkoxylated alkylamine surfactants of the present invention are described below.

Preferred polyethoxylated alkylamine surfactants of the present invention are alkylamines of formulae:

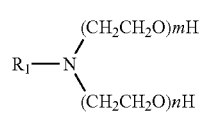

Formula IV

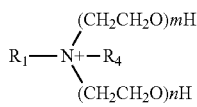

Formula V wherein $R_1$ is a $C_{8-20}$ branched alkyl, preferably a $C_{8-18}$ branched alkyl; $R_4$ is a, linear alkyl, a branched alkyl or a polyalkoxylate group (e.g., a polyethoxylate group, a polypropoxylate group or a copolymer of ethylene oxide and propylene oxide units); m and n independently are each from 2 to 20 and m+n totals 2 to about 25, preferably 10-1.5. When $R_4$ is present (thus creating an ion), the ion is neutralized by the glyphosate anion or a halogen (preferably chlorine).

A preferred surfactant of the present invention is a polyethoxylated alkylamine of Formula IV, wherein $R_1$ is a branched propylheptyl group. A particularly preferred surfactant of the present invention is a polyethoxylated alkylamine of Formula IV, wherein $R_1$ is a branched propylheptyl group (e.g., 2-propylheptyl), m is from 7 to 9 and n is from 7 to 9. Other branched propylheptyl groups are also useful as $R_1$ (e.g., 3-propylheptyl and 4-propylheptyl).

Preferred polypropoxylated or ethylene oxide-propylene oxide copolymer surfactants of the present invention include alkylamines of the following formulae:

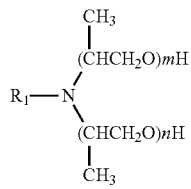

Formula VI

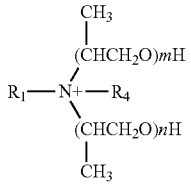

Formula VII

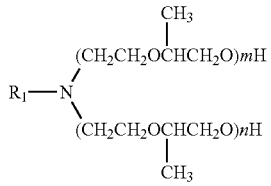

Formula VIII

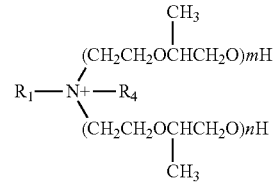

Formula IX

-continued

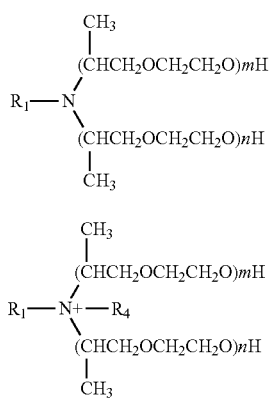
Formula X

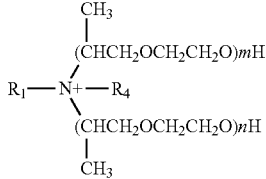
Formula XI wherein, in Formulae VI and VII, $R_1$ is a $C_{8-20}$ branched alkyl, preferably a $C_{8-18}$ branched alkyl; $R_4$ is a linear alkyl, a branched alkyl or, a polyalkoxylate group (e.g., a polyethoxylate group, a polypropoxylate group or a copolymer of ethylene oxide and propylene oxide units); m and n independently are each from 2 to 20 and m+n totals 2 to about 25, preferably 10-15; and wherein in Formulae VIII to XI, $R_1$ is a $C_{8-20}$ branched alkyl, preferably a $C_{8-18}$ branched alkyl; $R_4$ is a linear alkyl, a branched alkyl or a polyalkoxylate group (e.g., a polyethoxylate group, a polypropoxylate group or a copolymer of ethylene oxide and propylene oxide units); m and n independently are each from 1 to 10 and m+n totals 2 to about 12, preferably 5-8.

In Formulae VII, IX and XI, where $R_4$ is present (thus creating an ion), the ion is neutralized by the glyphosate anion or a halogen (preferably chlorine).

In all of the above Formulae, a preferred branched alkyl group $R_1$ is propylheptyl.

Other preferred polypropoxylated or ethylene oxide-propylene oxide copolymer surfactants of the present invention include those wherein the propylene oxide and/or ethylene oxide monomers are randomly distributed along the chain(s). Examples of such surfactants would be those having the following Formulae:

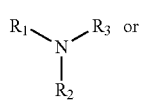
Formula XII

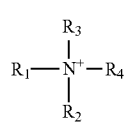
Formula XIII wherein $R_1$ is a $C_{8-20}$ branched alkyl, preferably a $C_{8-18}$ branched alkyl;

$R_2$ is a chain of from 2 to 20 ethylene oxide units and/or propylene oxide units selected from the group consisting of

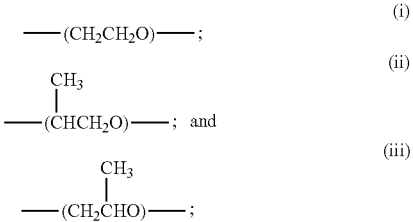

wherein said units are randomly distributed along the chain; $R_3$ is a linear alkyl, a branched alkyl or a polyalkoxylate group (e.g., a polyethoxylate, group, a polypropoxylate group or a copolymer of ethylene oxide and propylene oxide units, including a chain of from 2 to 20 ethylene oxide, units and/or propylene oxide units selected from the group consisting of:

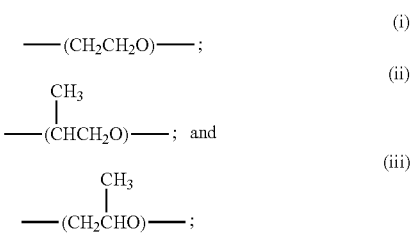

wherein said units are randomly distributed along the chain); $R_4$ is a linear alkyl, a branched alkyl or a polyalkoxylate group (e.g., a polyethoxylate group, a polypropoxylate group or a copolymer of ethylene oxide and propylene oxide units, including a chain of from 2 to 20 ethylene oxide units and/or propylene oxide units selected from the group consisting of (i) $\quad —(CH_2CH_2O)—;$ (ii) $\quad —(\underset{\underset{CH_3}{|}}{C}HCH_2O)—;$ and (iii) $\quad —(CH_2\underset{\underset{CH_3}{|}}{C}HO)—;$ wherein said units are randomly distributed along the chain); and when $R_4$ is present (thus creating an ion), the ion is neutralized by the glyphosate anion or a halogen (preferably chlorine).

In Formulae XII and XIII, the total number of ethylene oxide or propylene oxide units in $R_2$ and $R_3$ (combined) is preferably from 2 to 25, most preferably from 10 to 15.

The glyphosate herbicide of the present invention exhibits, among other things, an improved surface tension as compared to previously used glyphosate herbicides. The glyphosate herbicide of the present invention demonstrates improved rainfastness (better control of weeds in conditions where rain closely follows application of the herbicide) in comparison to other glyphosate herbicide formulations.

Another fundamental improvement made possible by these surfactants is the possibility to use a concentration of 450 g/liter of glyphosate or even higher, which reduces the cost and recycling of packages.

It is also possible to evaporate most of the water content of the solution in order to make a powder.

Example 1

We mixed the following quantities in a stirred reactor with a volume of 1.5 liters:

| | |
|---|---|
| Water | 445 g |
| Propylheptylamine polyethoxylated | 150 g |
| After the solution was prepared, we added | |
| Glyphosate 95% technical grade | 475 g |
| Isopropylamine | 130 g |
| Total | 1200 g/liter |

The propylheptylamine polyethoxylated surfactant used in this example had the structure of Formula I with $R_1$ being 2-propylheptyl and $R_2$ and $R_3$ being polyethoxylated chains with each having an average of eight (8) ethylene oxide monomers.

After total solution we measured the surface tension by the ring method (i.e., the Du Nouy method) of a 1% water solution and found 17 mN/m. This is a better surface tension than the typical value of 25-32 mN/m.

Field trials are underway.

Example 2

We mixed the following quantities in a stirred reactor with a volume of 1.5 liters:

| | |
|---|---|
| Water | 445 g |
| Propylheptylamine polypropoxylated | 150 g |
| After the solution was prepared, we added | |
| Glyphosate 95% technical grade | 475 g |
| Isopropylamine | 130 g |
| Total | 1200 g/liter |

The propylheptylamine polypropoxylated surfactant used in this example had the structure of Formula I with $R_1$ being 2-propylheptyl and $R_2$ and $R_3$ being polypropoxylated chains with each having an average of eight (8) propylene oxide monomers.

After total, solution we measured the surface tension by the ring method (i.e., the Du Nouy method) of a 1% water solution and found 18 mN/m. This is a better surface tension than the typical value of 25-32 mN/m.

Field trials are underway.

Example 3

A herbicide known as Madrigal 360 SL (360 grams/liter active) was applied to two separate stands of newly sprouted ryegrass at a dose rate of 1.5 liters per hectare (540 grams of active ingredient per hectare). Each of the stands of ryegrass was also irrigated (i.e., by spraying with artificial rain) with 5 mm of water (i.e., each stand of ryegrass was sprayed with an amount of water that simulated 5 mm of rainfall) after one hour. The efficacy of the Madrigal 360 SL herbicide was measured by observing the separate stands of ryegrass after two, three and four weeks from the initial application of the herbicide and noting the percentage of dead plants versus control stands that had not been exposed to the herbicide.

The results are shown in Table 1.

The Madrigal 360 SL herbicide contained glyphosate as the active ingredient and a surfactant which was a polyethoxylated amine with a linear alkyl group. The surfactant had the structure shown in Formula I with $R_1$ being octadecyl (i.e, linear $C_{18}H_{37}$) and $R_2$ and $R_3$ being polyethoxylated chains with each having an average of eight (8) ethylene oxide monomers.

Example 4

A herbicide known as Madrigal C 360 SL TAF (360 grams/liter active) was applied to two separate stands of newly sprouted ryegrass at a dose rate of 1.5 liters per hectare (540 grams of active ingredient per hectare). Each of the stands of ryegrass was also irrigated (i.e., by spraying with artificial rain) with 5 mm of water (i.e., each stand of ryegrass was sprayed with an amount of water that simulated 5 mm of rainfall) after one hour. The efficacy of the Madrigal C 360 SL TAF herbicide was measured by observing the separate stands of ryegrass after two, three, and four weeks from the initial application of the herbicide and noting the percentage of dead plants versus control stands that had not been exposed to the herbicide.

The results are shown in Table 1.

The Madrigal C 360 SL TAF herbicide contained glyphosate as the active ingredient and a surfactant which was a polyethoxylated amine with a branched alkyl group. The surfactant had the structure shown in Formula I with $R_1$ being propylheptyl (i.e., 2-propylheptyl) and $R_2$ and $R_3$ being polyethoxylated chains with each having an average of eight (8) ethylene oxide monomers.

TABLE 1

| Time after application | Madrigal C 360 SL TAF (360 grams active per liter) 540 grams active per hectare | Madrigal 360 SL (360 grams active per liter) 540 grams active per hectare | Roundup Max 540 grams active per hectare |
|---|---|---|---|
| 2 weeks | 12% | 7% | 2% |
| 3 weeks | 29% | 7% | 7% |
| 4 weeks | 40% | 7% | 10% |

The results shown in Table 1 demonstrate that the glyphosate herbicide formulations of the present invention, which use an alkyl amine surfactant having a branched alkyl group, are superior to comparable glyphosate herbicide formulations that use an alkyl amine surfactant having a linear alkyl group. The results also show that the glyphosate herbicide formulations of the present invention are markedly superior to a well-known and popular glyphosate herbicide formulation from the prior art (i.e., Roundup Max). For example, the glyphosate herbicide formulation of the present invention (i.e., Madrigal C 360 SL TAF) demonstrated a much better control of the target weed (ryegrass) when compared to: (1) a glyphosate herbicide formulation that used an alkyl amine surfactant having a linear alkyl group (i.e., Madrigal 360 SL); or (2) a glyphosate herbicide formulation from the prior art (i.e., Roundup Max); when all three formulations were tested under conditions which simulated rain shortly after application of the herbicide formulation. Thus, the glyphosate herbicide formulations of the present invention demonstrate a better rainfastness than the other glyphosate herbicide formulations.

Non-Limiting Recitation of Embodiments of the Invention

A herbicide consisting of a glyphosate formulation (i.e., glyphosate in water) containing as a surfactant an alkylamine polyethoxylated where the alkyl group is branched in order to reduce substantially the surface tension and improve efficacy of the formulation.

A herbicide consisting of a glyphosate formulation (i.e., glyphosate in water) containing as a surfactant an alkylamine polyethoxylated where the alkyl group is branched in order to reduce substantially the surface tension and improve efficacy of the formulation, wherein the alkyl group contains 6-14 carbon atoms which are not linear and may therefore include methyl, ethyl, propyl and/or butyl side groups.

A herbicide consisting of a glyphosate formulation (i.e., glyphosate in water) containing as a surfactant an alkylamine polyethoxylated where the alkyl group is branched in order to reduce substantially the surface tension and improve efficacy of the formulation, wherein the structure of the alkyl chain includes as main structure or side structure a cyclohexyl group (e.g., as part of the main chain of a branched alkyl group or as part of the branched portion of the branched alkyl group). Preferred branched alkyl groups containing a cyclohexyl group are 2, 3 or 4-cyclohexyl heptyl.

A herbicide consisting of a glyphosate formulation (i.e., glyphosate in water) containing as a surfactant an alkylamine polyethoxylated where the alkyl group is branched in order to reduce substantially the surface tension and improve efficacy of the formulation, wherein the number of ethylene oxide monomers in the polyethoxylated chain are 2 to 20, preferably 5 to 10.

A herbicide consisting of a glyphosate formulation (i.e., glyphosate in water) containing as a surfactant an alkylamine polyethoxylated where the alkyl group is branched in order to reduce substantially the surface tension and improve efficacy of the formulation, wherein the amine atom may be bound to one or two alkyl chains, where the third valence is connected to the polyethoxylated chain.

A herbicide consisting of a glyphosate formulation (i.e., glyphosate in water) containing as a surfactant an alkylamine polyethoxylated where the alkyl group is branched in order to reduce substantially the surface tension and improve efficacy of the formulation, wherein the pH of the formulation is increased above the isoelectric point of glyphosate in water by adding an alkaline metal hydroxide, or isopropylamine.

A herbicide consisting of a glyphosate formulation (i.e., glyphosate in water) containing as a surfactant an alkylamine polyethoxylated where the alkyl group is branched in order to reduce substantially the surface tension and improve efficacy of the formulation, wherein the formulation contains water, glyphosate, isopropyl amine or alkaline hydroxide and surfactant, and most or all of the water in the formulation is evaporated so as to convert the formulation into a powder.

A herbicide consisting of a glyphosate formulation (i.e., glyphosate in water) containing as a surfactant an alkylamine, wherein the nitrogen atom of the alkylamine is connected to polypropyleneoxide or to a copolymer of ethylene oxide and propylene oxide monomers, further wherein the alkyl group of the alkylamine is branched in order to reduce substantially the surface tension and improve efficacy of the formulation.

A herbicide consisting of a glyphosate formulation (i.e., glyphosate in water) containing as a surfactant an alkylamine, wherein the nitrogen atom of the alkylamine is connected to polypropylenoxide or to a copolymer of ethylene oxide and propylene oxide monomers, further wherein the alkyl group of the alkylamine is branched in order to reduce substantially the surface tension and improve efficacy of the formulation, and wherein the alkyl group contains 6-14 carbon atoms which are not linear and may therefore include methyl, ethyl, propyl and/or butyl side groups.

A herbicide consisting of a glyphosate formulation (i.e., glyphosate in water) containing as a surfactant an alkylamine, wherein the nitrogen atom of the alkylamine is connected to polypropylenoxide or to a copolymer of ethylene oxide and propylene oxide monomers, further wherein the alkyl group of the alkylamine is branched in order to reduce substantially the surface tension and improve efficacy of the formulation and wherein the structure of the alkyl chain includes as main structure or side structure a cyclohexyl group (e.g., as part of the main chain of a branched alkyl group or as part of the branched portion of the branched alkyl group). Preferred branched alkyl groups containing cyclohexyl group are 2, 3 or 4-cyclohexyl heptyl.

A herbicide consisting of a glyphosate formulation (i.e., glyphosate in water) containing as a surfactant an alkylamine; wherein the nitrogen atom of the alkylamine is connected to polypropylenoxide or to a copolymer of ethylene oxide and propylene oxide monomers, further wherein the alkyl group of the alkylamine is branched in order to reduce substantially the surface tension and improve efficacy of the formulation and wherein the number of ethylene oxide or propylene oxide monomers of the chain are 2 to 20, preferably 5 to 10.

A herbicide consisting, of a glyphosate formulation (i.e., glyphosate in water) containing as a surfactant an alkylamine, wherein the nitrogen atom of the alkylamine is connected to polypropyleneoxide or to a copolymer of ethylene oxide and propylene oxide monomers, further wherein the alkyl group of the alkylamine is branched in order to reduce substantially the surface tension and improve efficacy of the formulation and, wherein the proportion of ethylene oxide to propylene oxide monomers may vary from 0 to 100%.

A herbicide consisting of a glyphosate formulation glyphosate in water) containing as a surfactant an alkylamine, wherein the nitrogen atom of the alkylamine is connected to polypropyleneoxide or to a copolymer of ethylene oxide and propylene oxide monomers, further wherein the alkyl group of the alkylamine is branched in order to reduce substantially the surface tension and improve efficacy of the formulation and wherein the nitrogen atom of the amine may be bound to one or two alkyl chains, wherein the third valence is connected to the polyethoxylated or polypropoxylated chain.

A herbicide consisting of a glyphosate formulation (i.e., glyphosate in water) containing as a surfactant an alkylamine, wherein the nitrogen atom of the alkylamine is connected to polypropyleneoxide or to a copolymer of ethylene oxide and propylene oxide monomers, further wherein the alkyl group of the alkylamine is branched in order to reduce substantially the surface tension and improve efficacy of the formulation and wherein the pH of the formulation is increased above the isoelectric point of glyphosate in water by adding an alkaline metal hydroxide, or isopropylamine or an alkylamine containing 3-7 carbon atoms or a mixture of amines.

A herbicide consisting of a glyphosate formulation (i.e., glyphosate in water) containing as a surfactant an alkylamine, wherein the nitrogen atom of the alkylamine is, connected to polypropyleneoxide or to a copolymer of ethylene oxide and propylene oxide monomers, further wherein the alkyl group of the alkylamine is branched in order to reduce substantially the surface tension and improve efficacy of the formulation and wherein the formulation contains water, glyphosate, alkyl amine or alkaline hydroxide and surfactant, and most or all of the water in the formulation is evaporated so as to convert the formulation into a powder.

A herbicide comprising a glyphosate formulation containing as, a surfactant an alkylamine of Formula I or II:

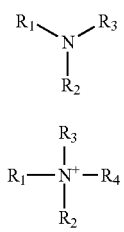

wherein $R_1$ is a $C_{8-20}$ branched alkyl, preferably a $C_{8-18}$ branched alkyl;

$R_2$ is a polyalkoxylate group, preferably a polyethoxylate group, a polypropoxylate group or a copolymer of ethylene oxide and propylene oxide monomers (e.g., a polyethoxylate group; or a polypropoxylate group; or a polyethoxylate group containing from 2 to 20 ethylene oxide monomers; or a polyethoxylate group containing from 5 to 10 ethylene oxide monomers; Or a polypropoxylate group containing from 1 to 20 propylene oxide monomers; or a polypropoxylate group containing from 5 to 10 propylene oxide monomers; or a copolymer of ethylene oxide and propylene oxide monomers forming a chain containing from 2 to 20 total monomers, wherein said ethylene oxide and propylene oxide monomers may be randomly distributed along said chain);

$R_3$ is a linear alkyl, a branched alkyl or a polyalkoxylate group;

$R_4$ is a linear alkyl, a branched alkyl or a polyalkoxylate group; and when $R_4$ is present (thus creating an ion), the ion is, neutralized by the glyphosate anion or a halogen (preferably chlorine).

A herbicide comprising:
(a) glyphosate;
(b) water;
(c) a surfactant; and
(d) a pH modifier;
wherein said pH modifier is an alkaline metal hydroxide, an amine or a mixture of amines (e.g., an alkylamine containing from 3-7 carbon atoms, such as isopropylamine, or a mixture of alkylamines containing from 3-7 carbon atoms), and the pH modifier increases the pH of the herbicide to a point above the isoelectric point of glyphosate in water; and
further wherein said surfactant contains an alkylamine of Formula I or II:

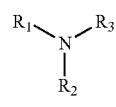

wherein $R_1$ is a $C_{8-20}$ branched alkyl, preferably a $C_{8-18}$ branched alkyl;

$R_2$ is a polyalkoxylate group, preferably a polyethoxylate group, a polypropoxylate group or a copolymer of ethylene oxide and propylene oxide monomers (e.g., a polyethoxylate group; or a polypropoxylate group; or a polyethoxylate group containing from 2 to 20 ethylene, oxide monomers; or a polyethoxylate group containing from 5 to 10 ethylene oxide monomers; or a polypropoxylate group containing from 2 to 20 propylene oxide monomers; or a polypropoxylate group containing from 5 to 10 propylene oxide monomers; or a copolymer of ethylene oxide and propylene oxide monomers forming a chain containing from 2 to 20 total monomers, wherein said ethylene oxide, and propylene oxide Monomers may be randomly distributed along said chain);

$R_3$ is a linear alkyl, a branched alkyl or a polyalkoxylate group;

$R_4$ is a linear alkyl, a branched alkyl or a polyalkoxylate group; and when $R_4$ is present (thus creating an ion), the ion is neutralized by the glyphosate anion or a halogen (preferably chlorine).

The herbicide of the present invention can be in the form of an aqueous solution or in the form of a powder (e.g., the aqueous solution with most or all of the water removed).

A herbicide comprising a glyphosate formulation containing as a surfactant an alkylamine of Formula IV

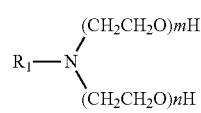

wherein $R_1$ is a 2-propylheptyl group;
m is 8 in the average; and
n is 8 in the average.

A herbicide comprising a glyphosate formulation containing as a surfactant an alkylamine of Formula VI

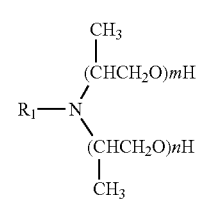

wherein $R_1$ is a 2-propylheptyl group;
m is 8 in the average; and
n is 8 in the average.

A herbicide comprising;
(a) glyphosate;
(b) water;
(c) a surfactant; and
(d) a pH modifier;
wherein said pH modifier is isopropylamine and the amount of isopropylamine used increases the pH of the herbicide to a point above the isoelectric point of glyphosate in water;

further wherein said surfactant contains an alkylamine of Formula VI

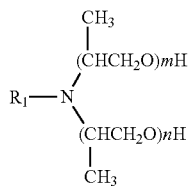

Formula VI wherein $R_1$ is a 2-propylheptyl group;

m is 8 in the average; and n is 8 in the average.

A herbicide comprising:
(a) glyphosate;
(b) water;
(c) a surfactant; and
(d) a pH modifier;

wherein said pH modifier is isopropylamine and the amount of isopropylamine used increases the pH Of the herbicide to a point above the isoelectric point of glyphosate in water;

further wherein said surfactant contains an alkylamine of Formula IV

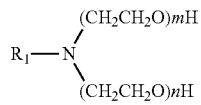

Formula IV wherein $R_1$ is a 2-propylheptyl group;
m is 8 in the average; and
n is 8 in the average.

What is claimed is:

1. A herbicide comprising a glyphosate formulation containing as a surfactant a branched alkyl amine polyalkoxylated of formula

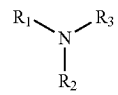

wherein
$R_1$ is selected from the group consisting of 2-propyl heptyl or 3-propyl heptyl
$R_2$ and $R_3$ are selected from the group consisting of polyethoxylate, polypropoxylate or a copolymer of ethylene oxide and propylene oxide containing 2-20 monomers.

2. The herbicide of claim 1, wherein the herbicide further comprises water and a pH modifier.

* * * * *